(12) United States Patent
Trautman et al.

(10) Patent No.: US 6,855,372 B2
(45) Date of Patent: Feb. 15, 2005

(54) METHOD AND APPARATUS FOR COATING SKIN PIERCING MICROPROJECTIONS

(75) Inventors: Joseph C. Trautman, Sunnyvale, CA (US); Cedric T. Wright, Santa Clara, CA (US); Michel J. N. Cormier, Mountain View, CA (US)

(73) Assignee: ALZA Corporation, Mountain View, CA (US)

( * ) Notice: Subject to any disclaimer, the term of this patent is extended or adjusted under 35 U.S.C. 154(b) by 240 days.

(21) Appl. No.: 10/099,604

(22) Filed: Mar. 15, 2002

(65) Prior Publication Data

US 2002/0132054 A1 Sep. 19, 2002

Related U.S. Application Data

(60) Provisional application No. 60/351,586, filed on Jan. 22, 2002, provisional application No. 60/276,762, filed on Mar. 16, 2001, and provisional application No. 60/342,550, filed on Dec. 20, 2001.

(51) Int. Cl.$^7$ ............................................. B05D 5/00
(52) U.S. Cl. ................... 427/287; 427/256; 427/2.31
(58) Field of Search ................. 427/2.1, 2.14, 427/2.31, 287, 256, 428, 429, 430.1, 434.3; 101/490

(56) References Cited

U.S. PATENT DOCUMENTS

| | | | |
|---|---|---|---|
| 3,136,314 A | 6/1964 | Kravits | 128/253 |
| RE25,637 E | 9/1964 | Kravitz et al. | 128/253 |
| 3,351,059 A | 11/1967 | Kravitz | 128/253 |
| 3,814,097 A | 6/1974 | Ganderton et al. | 128/268 |
| 3,964,482 A | 6/1976 | Gerstel et al. | 128/260 |
| 4,109,655 A | 8/1978 | Chacornac | 128/253 |
| 4,453,926 A | 6/1984 | Galy | 604/47 |
| 5,213,839 A * | 5/1993 | Awazu et al. | |
| 5,250,023 A | 10/1993 | Lee et al. | 604/20 |
| 5,279,544 A | 1/1994 | Gross et al. | 604/20 |
| 5,487,726 A | 1/1996 | Rabenau et al. | 604/46 |
| 5,797,991 A * | 8/1998 | Boockman | |
| 6,050,988 A | 4/2000 | Zuck | 604/890.1 |
| 6,083,196 A | 7/2000 | Trautman et al. | 604/46 |
| 6,091,975 A | 7/2000 | Daddona et al. | 600/345 |
| 6,117,480 A * | 9/2000 | Spallek et al. | |

FOREIGN PATENT DOCUMENTS

| | | | |
|---|---|---|---|
| EP | 0 407 063 A1 | 1/1991 | A61B/17/20 |
| WO | WO 96/17648 | 11/1996 | A61N/1/30 |
| WO | WO 96/37155 | 11/1996 | A61B/17/20 |
| WO | WO 97/37256 | 11/1996 | A61N/1/30 |
| WO | WO 97/03718 | 2/1997 | A61M/27/00 |
| WO | WO 97/48440 | 12/1997 | A61N/1/30 |
| WO | WO 97/48441 | 12/1997 | A61N/1/30 |
| WO | WO 97/48442 | 12/1997 | A61N/1/30 |
| WO | WO 98/00193 | 1/1998 | A61M/31/00 |
| WO | WO 98/11937 | 3/1998 | A61M/37/00 |
| WO | WO 98/28037 | 7/1998 | A61M/37/00 |
| WO | WO 99/29298 | 6/1999 | A61M/37/00 |
| WO | WO 99/29365 | 6/1999 | A61M/1/30 |
| WO | WO 99/64580 | 12/1999 | C12N/15/00 |

* cited by examiner

*Primary Examiner*—Brenda A. Lamb

(57) ABSTRACT

An apparatus and method are provided for selectively applying an agent-containing liquid coating to extremely tiny skin piercing microprojections (10). The coating solution is applied to the skin piercing microprojections (10) using a coating technique which selectively coats only the skin piercing microprojections (10) and not the substrate (12) from which the microprojections (10) extend, and then dried. The coating method includes providing an agent-containing coating liquid and conveying the liquid to a liquid holding surface having a coating transfer region. The depth of the coating liquid at the coating transfer region is precisely controlled. The microprojections are then immersed to a predetermined level in the coating liquid. The liquid that coats the microprojections (10) is then dried to form a solid agent-containing coating on the microprojections (10).

12 Claims, 9 Drawing Sheets

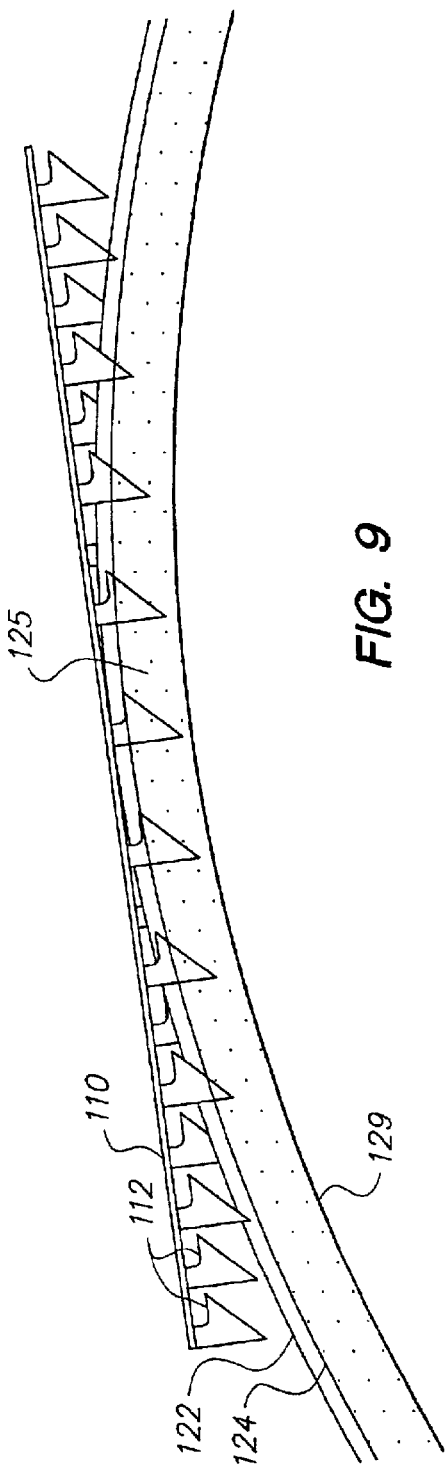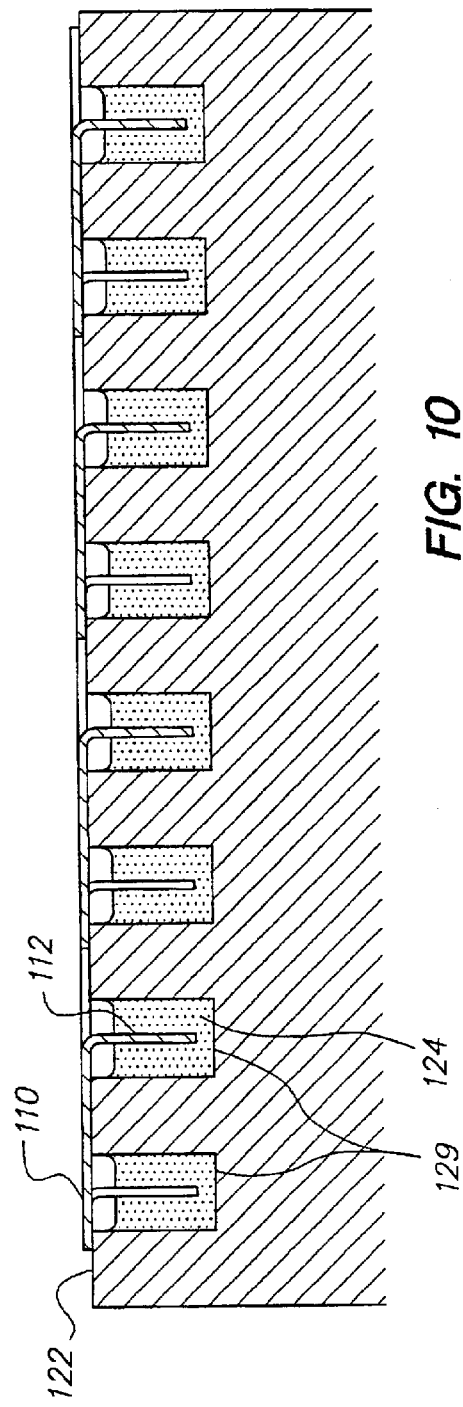

METHOD AND APPARATUS FOR COATING SKIN PIERCING MICROPROJECTIONS

CROSS REFERENCE TO RELATED APPLICATIONS

Priority is claimed under 35 U.S.C. 119(e) from U.S. Provisional Patent Applications Ser. Nos. 60/276,762 filed Mar. 16, 2001; 60/342,550 filed Dec. 20, 2001; and 60/351,586 filed Jan. 22, 2002.

TECHNICAL FIELD

This invention relates to administering and enhancing delivery of an agent into or through the skin. More particularly, the invention relates to a method and apparatus for making a percutaneous drug delivery system for administering therapeutic active agent (i.e., a drug or vaccine) into or through the skin using skin piercing microprojections which have a dry coating of the agent. Delivery of the agent is facilitated when the microprojections pierce the skin of a patient and the patient's body fluid contacts and dissolves the active agent. Even more particularly, the invention relates to a method and apparatus for selectively coating the agent on the microprojections.

BACKGROUND ART

Transdermal drug delivery systems generally rely on passive diffusion to administer the drug while active transdermal drug delivery systems rely on an external energy source (e.g., electricity) to deliver the drug. Passive transdermal drug delivery systems are more common. Passive transdermal systems have a drug reservoir containing a high concentration of drug adapted to contact the skin where the drug diffuses through the skin and into the body tissues or bloodstream of a patient. The transdermal drug flux is dependent upon the condition of the skin, the size and physical/chemical properties of the drug molecule, and the concentration gradient across the skin. Because of the low skin permeability to many drugs, transdermal delivery has had limited applications. This low permeability is attributed primarily to the stratum corneum, the outermost skin layer which consists of flat, dead cells filled with keratin fibers (keratinocytes) surrounded by lipid bilayers. The highly-ordered structure of the lipid bilayers confers a relatively impermeable character to the stratum corneum.

One method of increasing the passive transdermal diffusional drug flux involves mechanically penetrating or disrupting the outermost skin layers thereby creating pathways into the skin in order to enhance the amount of agent being transdermally delivered. Early vaccination devices known as scarifiers generally had a plurality of tines or needles which are applied to the skin to and scratch or make small cuts in the area of application. The vaccine was applied either topically on the skin, as disclosed in Rabenau, U.S. Pat. No. 5,487,726 or as a wetted liquid applied to the scarifier tines as disclosed in Galy, U.S. Pat. No. 4,453,926, Chacornac, U.S. Pat. No. 4,109,655, and Kravitz, U.S. Pat. No. 3,136,314 or as a dry coating on and between the scarifier tines as disclosed in Kravitz U.S. Pat. No. 3,351,059. Scarifiers have been suggested for intradermal vaccine delivery in part because only very small amounts of the vaccine need to be delivered into the skin to be effective in immunizing the patient. Further, the amount of vaccine delivered is not particularly critical since an excess amount achieves satisfactory immunization as well as a minimum amount. However a serious disadvantage in using a scarifier to deliver a drug is the difficulty in determining the transdermal drug flux and the resulting dosage delivered. Also due to the elastic, deforming and resilient nature of skin to deflect and resist puncturing, very tiny (e.g., having lengths less than about 0.5 mm) skin piercing elements often do not uniformly penetrate the skin and/or are wiped free of a coating, particularly a liquid coating, of an agent upon skin penetration. Additionally, due to the self healing process of the skin, the punctures or slits made in the skin tend to close up after removal of the piercing elements from the stratum corneum. Thus, the elastic nature of the skin acts to remove active agent coating the tiny piercing elements upon penetration. Furthermore the tiny slits formed by the piercing elements heal quickly after removal of the device, thus, limiting the passage of agent through the passageways created by the piercing elements and in turn limiting the transdermal flux of such devices.

Other devices which use tiny skin piercing elements to enhance transdermal drug delivery are disclosed in European Patent EP 0407063A1, Godshall, et al. U.S. Pat. No. 5,879,326; Ganderton, et al. U.S. Pat. No. 3,814,097; Gross, et al. U.S. Pat. No. 5,279,544; Lee, et al. U.S. Pat. No. 5,250,023; Gerstel, et al. U.S. Pat. No. 3,964,482; Kravitz, et al. U.S. Pat. No. Reissue 25,637 and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated by reference in their entirety. These devices use piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having dimensions (i.e., a microprojection length and width) of only about 25–400 $\mu$m and a mircorprojection thickness of only about 5–50 $\mu$m. These tiny piercing/cutting elements make correspondingly small microslits/microcuts in the stratum corneum for enhanced transdermal agent delivery therethrough.

More recently, Cormier et al., in U.S. patent application Ser. No. 10/045,842 filed Oct. 26, 2001 disclose a device for transdermally delivering a potent drug. The device has a plurality of skin piercing microprojections which have a dry coating of the drug. Cormier et al. disclose microfluidic coating techniques such as ink jet printing to selectively coat the drug only on the skin piercing microprojections rather than on other portions/surfaces of the device which do not penetrate into the skin. In spite of these disclosures, Cormier et al. do not address the difficulties in aiming the microfluidic spray or deposit only onto the portions of the device which pierce the skin. Thus, there is a need for a precisely controlled coating method which can reproducibly, and at high volumes, coat only the skin-piercing portions of such devices.

DISCLOSURE OF THE INVENTION

The apparatus and method of the present invention overcome these difficulties by providing a coating liquid of precisely controlled depth and conveying, in a precisely controlled manner the microprojections through the coating liquid. The method of the present invention is useful for coating a liquid onto a plurality of microprojections extending from a surface or edge of a substrate without coating the liquid onto the substrate itself. The method includes providing an agent-containing coating liquid and conveying the liquid onto a liquid-holding surface having a coating transfer region. The depth of the coating liquid on the coating transfer region is precisely controlled to a predetermined depth. The microprojections are immersed to a predetermined level in the coating liquid at the coating transfer region. The depth of the coating liquid in the coating transfer region should be at least slightly greater than the level of immersion of the microprojections, as measured perpendicularly from the substrate surface or edge. The microprojections are most typically immersed only partially in the coating liquid so that only a portion of the entire length of the microprojections is coated. After coating, the microprojections are removed from the coating liquid and then dried thereby forming a dry agent-containing coating on the microprojections. An important advantage of the present invention is that for very expensive agents (e.g., expensive drugs or vaccines), the agent is coated only on those portions of the device which pierce into the skin, i.e., only the microprojections and not the substrate is coated with the agent.

The apparatus of the present invention is suitable for coating an agent-containing liquid onto a plurality of microprojections extending from a surface or edge of a substrate substantially without coating the substrate. The apparatus includes a liquid holding surface having a coating transfer region. The liquid holding surface can be either curved or flat. A liquid conveyor conveys the coating liquid to the coating transfer region. A coating thickness controller controls the thickness of the coating at the coating transfer region to a precisely predetermined thickness. A positionably adjustable substrate conveyer conveys the microprojections past the coating transfer region such that the microprojections are immersed to a predetermined depth level in the coating liquid.

In one embodiment, the liquid holding surface is the cylindrically-shaped outer surface of a rotatable roller or drum. The coating liquid is conveyed to a coating transfer region by rotating the roller or drum through a bath of the coating liquid. The coating thickness controller can be either a doctor blade and/or a second roller substantially parallel with the liquid conveying roller or drum and spaced a predetermined distance therefrom.

In a second embodiment, the liquid holding surface, either curved or flat, is substantially immobile and the coating liquid flows e.g., by force of gravity, thereover.

The substrate conveyer can take any of several forms. In one embodiment, the substrate conveyer comprises a track which is positionally adjustable relative to the coating transfer region. A substrate holding sled runs along the track past the coating transfer region.

In a second embodiment, the substrate conveyer continuously conveys a web comprised of a plurality of substrates past the coating transfer region. The continuous substrate conveyer can include a substrate web supply roll and a take-up roll with a positionally adjustable web guide therebetween for positioning the continuous web relative to the coating transfer region.

Preferably, the agent is sufficiently potent to be therapeutically effective in a dose of less than about 1 mg, and preferably less than about 0.25 mg, per application. Preferably, the agent has a water solubility of greater than about 50 mg/ml, and more preferably greater than about 100 mg/ml. The liquid coating solution or suspension typically has a viscosity of about 5 to 500 centipoise (cP), more typically about 20 to 50 cP, when measured at a temperature of 25° C. and a shear strain rate of 100 $sec^{-1}$. The thickness of the solid (i.e., after drying) coating on the microprojections is preferably less than the thickness of the microprojections, more preferably the thickness is less than 25 $\mu$m and most preferably less than 10 $\mu$m. Generally, the coating thickness is an average thickness measured over the surfaces of the microprojections.

The agent for coating the microprojections is selected to have sufficient potency to be therapeutically effective when administered transdermally in an amount of less than about 1 mg, and preferably less than about 0.25 mg, of active agent. The most preferred agents are vaccines and potent drugs. Preferred potent drugs include ACTH (1–24), calcitonin, desmopressin, LHRH, LHRH analogs, goserelin, leuprolide, PTH, vasopressin, deamino [Val4, D-Arg8] arginine vasopressin, buserelin, triptorelin, interferon alpha, interferon beta, interferon gamma, FSH, EPO, GM-CSF, G-CSF, IL-10, glucagon and analogs of these agents including pharmaceutically acceptable salts thereof.

BRIEF DESCRIPTION OF THE DRAWINGS

The invention will now be described in greater detail with reference to the preferred embodiments illustrated in the accompanying drawings and figures wherein:

FIG. 9 is a side sectional view of another coating apparatus of the present invention;

FIG. 10 is an end sectional view of the apparatus shown in FIG. 9;

MODES FOR CARRYING OUT THE INVENTION

The term "transdermal" means the delivery of an agent (e.g., a drug or vaccine) into and/or through the skin for local or systemic therapy.

The term "transdermal flux" means the rate of transdermal delivery.

The term "microprojections" refers to piercing elements which are adapted to pierce or cut through the stratum corneum into the underlying epidermis layer, or epidermis and dermis layers, of the skin of a living animal, particularly a human. The piercing elements should not pierce the skin to a depth which causes bleeding. Typically the piercing elements have a blade length of less than 500 μm, and preferably less than 250 μm. The microprojections typically have a width of about 75 to 500 μm and a thickness of about 5 to 50 μm. The microprojections may be formed in different shapes, such as needles, hollow needles, blades, pins, punches, and combinations thereof.

The term "microprojection array" as used herein refers to a plurality of microprojections arranged in an array for piercing the stratum corneum. The microprojection array may be formed by etching or punching a plurality of microprojections from a thin sheet and folding or bending the microprojections out of the plane of the sheet to form a configuration such as that shown in FIG. 1. The microprojection array may also be formed in other known manners, such as by forming one or more strips having microprojections along an edge of each of the strip(s) as disclosed in Zuck, U.S. Pat. No. 6,050,988. The microprojection array may include hollow needles which hold a dry pharmacologically active agent.

The present invention provides an apparatus and method for selectively applying an agent-containing liquid on the skin piercing portions of a microprojection device having a plurality of stratum corneum-piercing microprojections extending therefrom in order to form an agent-containing coating on the microprojections. The liquid-coated microprojections are then dried to form a solid coating thereon which contains the agent. The microprojections are adapted to pierce through the stratum corneum into the underlying epidermis layer, or epidermis and dermis layers, but do not penetrate so deep as to reach the capillary beds and cause significant bleeding. Typically, the microprojections have a length which allows skin penetration to a depth of up to about 500 μm, and preferably up to about 400 μm. Upon piercing the stratum corneum layer of the skin, the agent-containing coating is dissolved by body fluid (intracellular fluids and extracellular fluids such as interstitial fluid, blood, or mixtures thereof) and released into the skin for local or systemic therapy.

Figure 1:
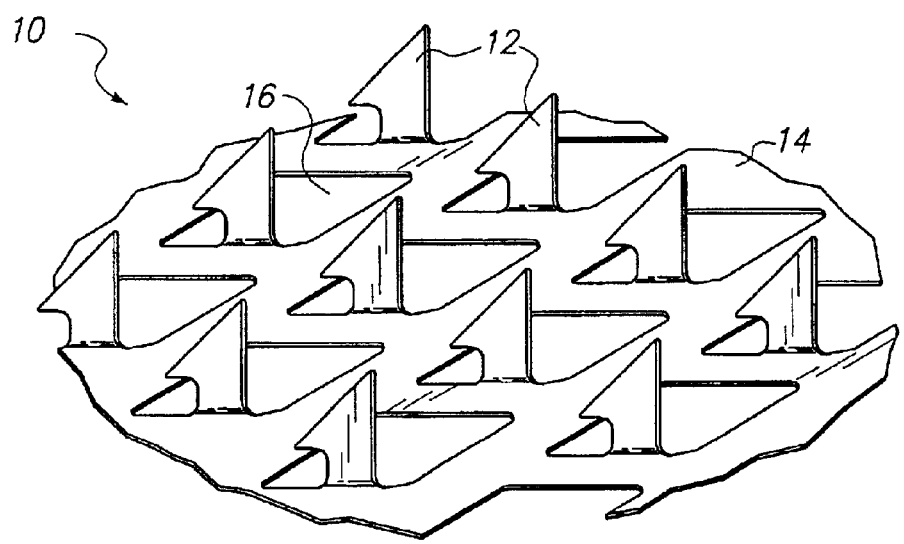
FIG. 1 is a perspective view of a portion of one example of a microprojection array.
Figure 8:
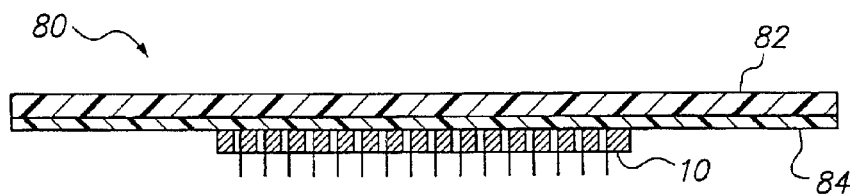
FIG. 8 is a side sectional view of an intradermal agent delivery system having a microprojection member with microprojections which are coated using the present invention.

FIG. 1 illustrates one embodiment of stratum corneum-piercing microprojection member 10 for use with the present invention. FIG. 1 shows a portion of the member 10 having a plurality of microprojections 12. The microprojections 12 extend at substantially a 90° angle from a sheet 14 having openings 16. The member 10 may be incorporated in an agent delivery or sampling system 80 (shown in FIG. 8) including a backing 82 and adhesive 84 for adhering the system 80 to the skin. In the embodiment of the microprojection member 10 shown in FIGS. 1, 2 and 8, the microprojections 12 are formed by etching or punching a plurality of microprojections 12 from a thin metal sheet 14 and bending the microprojections 12 out of a plane of the sheet. Metals such as stainless steel and titanium are preferred. Metal microprojection members and methods of making same are disclosed in Trautman et al, U.S. Pat. No. 6,083,196; Zuck U.S. Pat. No. 6,050,988; and Daddona et al., U.S. Pat. No. 6,091,975 the disclosures of which are incorporated herein by reference. Other microprojection members that can be used with the present invention are formed by etching silicon using silicon chip etching techniques or by molding plastic using etched micro-molds. Silicon and plastic microprojection members are disclosed in Godshall et al. U.S. Pat. No. 5,879,326, the disclosures of which are incorporated herein by reference.

Figure 2:
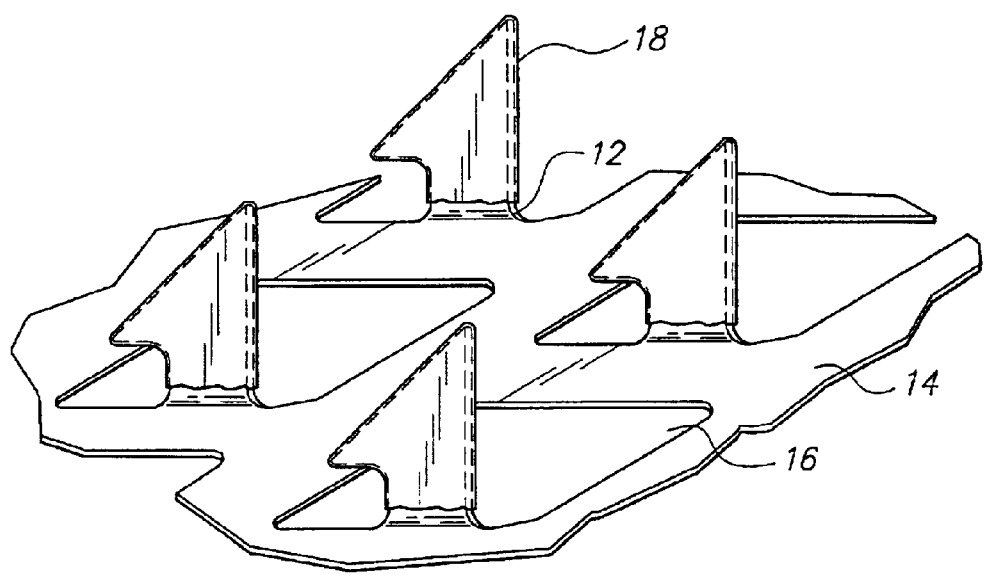
FIG. 2 is a perspective view of the microprojection array of FIG. 1 with a coating deposited onto the microprojections.

FIG. 2 illustrates the microprojection member 10 having microprojections 12 having a pharmacologically active agent-containing coating 18. The coating 18 may partially or completely cover the microprojections 12.

Figure 3:
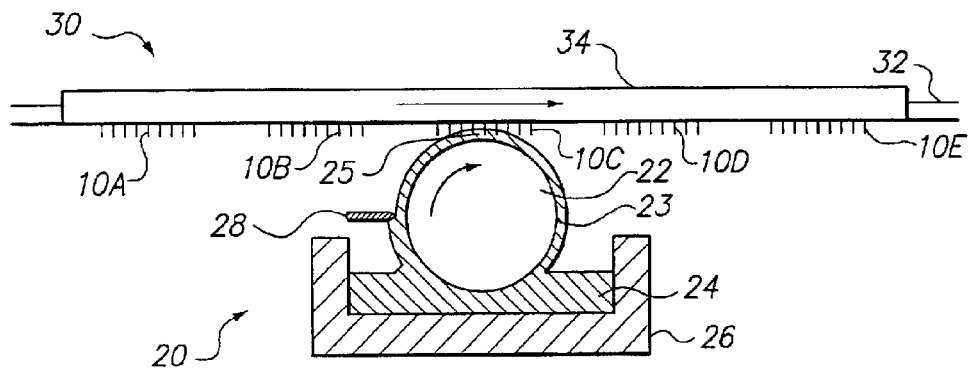
FIG. 3 is a side schematic view of one embodiment of the apparatus according to the present invention.

In accordance with the present invention, the agent-containing coating is applied after the microprojections 12 are formed (i.e., etched) and bent out of the plane of metal sheet 14. The coating on the microprojections 12 is formed by a dip-coating using the apparatuses shown in FIGS. 3 through 7, 9 and 10. FIG. 3 discloses one embodiment of a microprojection member coating apparatus 20 in accordance with the present invention. Coating apparatus 20 includes a rotating drum 22 partially immersed in a bath of coating liquid 24. The coating liquid 24 is contained within open container 26. Drum 22 rotates in a clockwise manner as shown by the arrow. The liquid 24 is picked up by the surface of the rotating drum as it rotates through the bath. A doctor blade 28 is provided to control the thickness of the coating liquid downstream from the doctor blade. Thus, the outer surface 23 of the rotating drum acts as a coating liquid holding surface which transfers the coating liquid to the coating transfer region 25 located at approximately the 12 o'clock position of the rotating drum 22.

The material used for the drum 22, or any surface treatment thereof, will be somewhat dependent on the particular liquid 24 being coated. Those skilled in the art will appreciate that the coating liquid must be able to wet the surface of drum 22. For aqueous protein coating solutions, a drum made of Delrin®, an acetal resin sold by E.I. DuPont de Nemours and Co. of Wilmington, Del. has been found to work well.

Similarly, the drum surface speed (i.e., the circumference of the drum multiplied by the drum rotational speed) will also be somewhat dependent upon the particular liquid 24 being coated. Drum surface speeds of about 20 to 150 cm/minute (10 to 60 inches/minute) are typically used, while drum speeds of 50 to 75 cm/minute (20 to 30 inches/minute) have been found to be most useful for coating aqueous protein solutions.

Positioned above the rotating drum 22 is a microprojection member conveyor 30. Conveyor 30 includes a track 32 on which rides one or more sleds 34. Sled 34 has a plurality of microprojection members 10a, 10b, 10c, 10d, and 10e mounted thereon. The position of the track 32 relative to the top of the rotating drum 22 is precisely controlled using micrometer-like position adjusting elements (not shown in FIG. 3). The sled 34 is adapted to move on track 32 from left to right as shown by the arrow. As the microprojection members 10e, 10d, and 10c pass over the rotating drum 22, the microprojections are coated by the coating liquid 24 in the coating transfer region 25. Preferably the rotational speed of drum 22 is controlled so that the speed of the outer surface of drum 22 approximately matches the speed of sled 34 moving along track 32. In this way, there is essentially no wake created in the coating transfer region 25 by the microprojection members 10 moving through region 25. This is important in preventing any ripples/waves in the surface of the coating liquid in the coating transfer region 25 which could otherwise cause coating of the sheet 14 (see FIG. 1) of the microprojection members 10 or a difference in coating length between the upstream and downstream sides of the microprojections.

Figure 4:
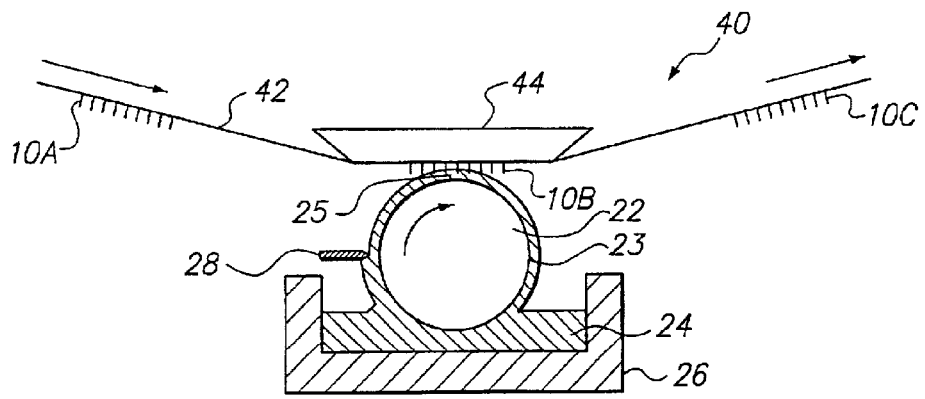
FIG. 4 is a side schematic view of another apparatus according to the present invention.
Figure 6:
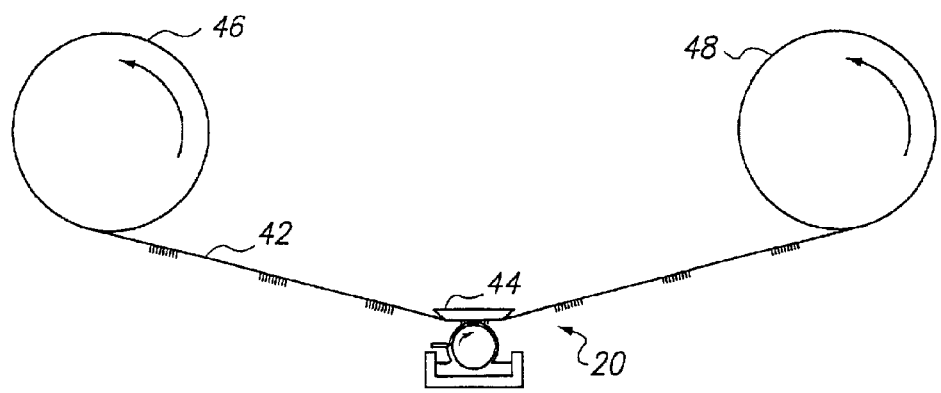
FIG. 6 is a side perspective view showing a continuous substrate conveyor in accordance with one embodiment of the present invention.

FIG. 4 and 6 illustrate an alternate microprojection member conveyor 40. In this embodiment, the microprojection members 10a, 10b, and 10c are part of a continuous web 42. The web 42 is fed continuously under anvil 44 which, like track 32, is precisely positionable with respect to the outer surface of the rotating drum 22. In a more preferred embodiment, the microprojection member web conveyor 40 may include a web supply roll 46 and a web take-up roll 48 as shown in FIG. 6. The microprojections may optionally be punched (i.e., bent) out of the plane of the web 42 at a punching station (not shown in FIG. 6) positioned between the supply roll 46 and the anvil 44. Optionally, the coated individual microprojection members 10 can be punched out of web 42 downstream of anvil 44 and before takeup of the excess web on take-up roll 48.

Figure 5:
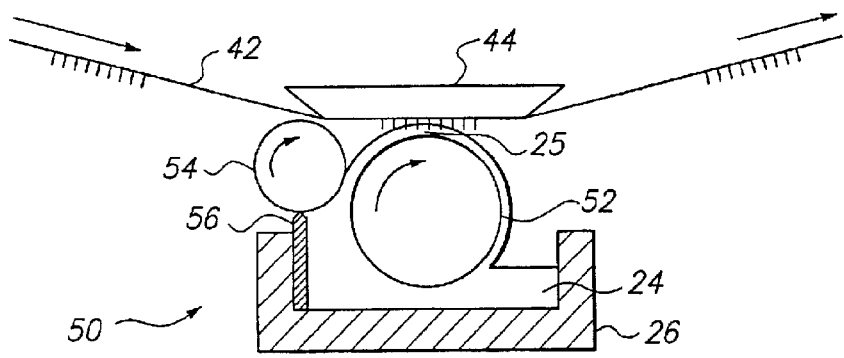
FIG. 5 is a side schematic view of yet another apparatus according to the present invention.

The microprojection member coating apparatus 50 shown in FIG. 5 is similar to the coating apparatus shown in FIG. 4 with the following differences. The rotating coating drum 52 has a coating thickness controller in the form of a parallel secondary roller 54 spaced a predetermined distance therefrom. A wiping blade 56 wipes the surface of secondary roller 54 so that the surface of roller 54 is substantially liquid free as it enters the nip between the rotating drum 52 and the secondary roller 54. In this manner, a coating liquid of precisely controlled thickness is provided on the surface of rotating drum 52 upstream from the nip between secondary roller 54 and drum 52. In this manner, the thickness of the coating liquid in the coating transfer region 25 is precisely controlled. A microprojection member conveyor including an adjustably positionable anvil 44 and a continuous web of microprojection members 42 is conveyed past the coating transfer region 25 in the direction of the arrows. Thus, the direction of web 42 is substantially the same as the rotational direction of rotating drum 52 with the speeds thereof roughly matched in order to prevent waves and ripples in the coating liquid in region 25.

Figure 13:
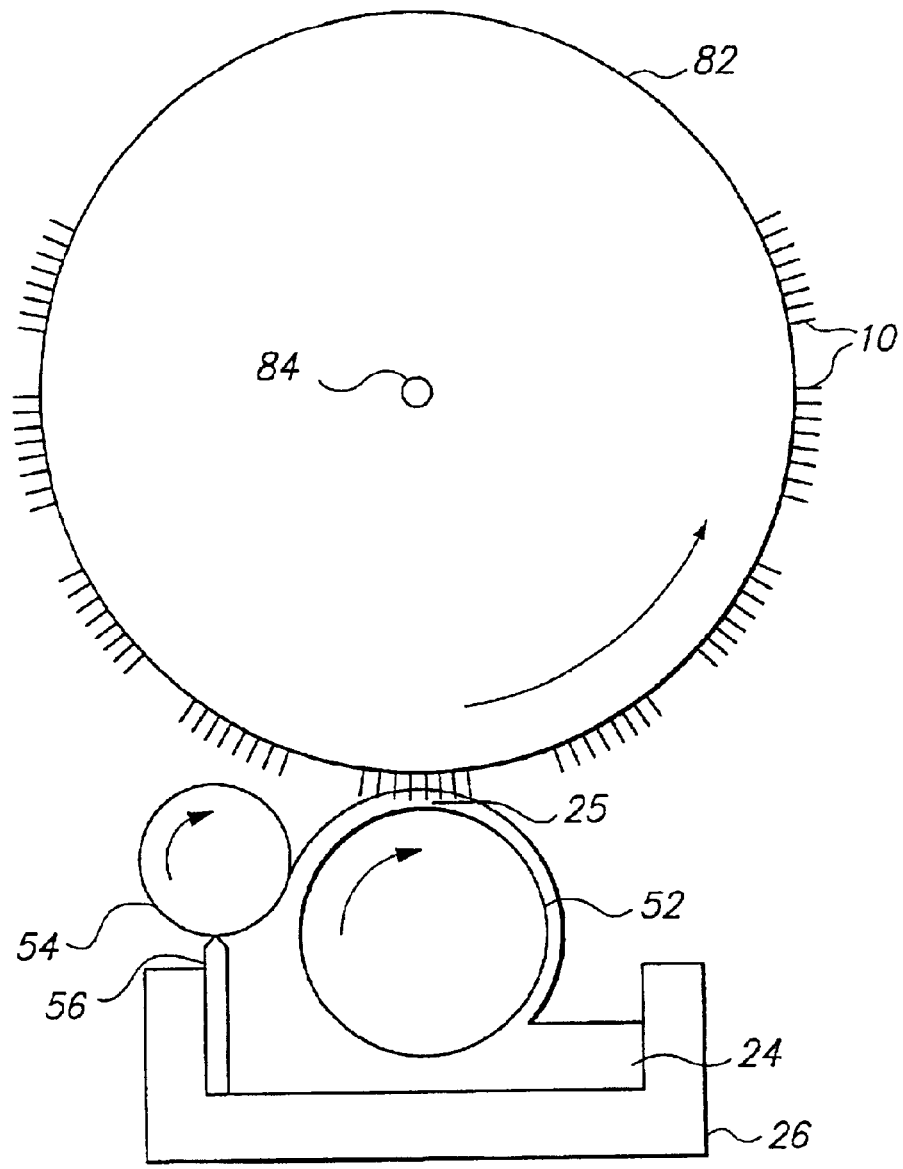
FIG. 13 is a side schematic view of another embodiment of the apparatus of the invention.

FIG. 13 discloses an alternate microprojection member coating apparatus 80 similar to the apparatus shown in FIG. 5 but having a different microprotrusion member conveyor. The microprotrusion member conveyor of apparatus 80 comprises a drum 82 having removably mounted thereon a plurality of microprojection members 10. The mounting of members 10 on the cylindrical surface of drum 82 can be done by conventional means, including having a hollow drum 82 with small openings on the cylindrical surface through which a partial vaccum is drawn, using magnets (in the case of ferro metallic members 10) and other known non-permanent mounting means. Drum 82 is adapted to rotate around axis 84 as shown by the arrow. As drum 82 rotates about axis 84, the microprojections of members 10 are sequentially conveyed through coating transfer region 25. The depth of the coating liquid 24 in coating transfer region 25 is controlled as is previously described in connection with the apparatus 50 of FIG. 5. This apparatus enables the microprojection members to be coated multiple times without operator intervention. Although FIG. 13 shows a cylindrically shaped drum 82 having the microprojection members 10 mounted thereon, those skilled in the art will appreciate that only a partial cylindrical surface is necessary in order to coat according to the method illustrated in FIG. 13.

Figure 7:
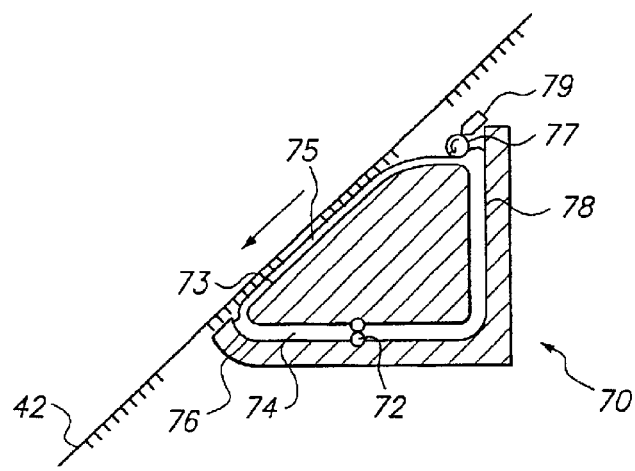
FIG. 7 is a side view, shown partly in section, of a portion of the coating apparatus of the present invention.

FIG. 7 discloses an alternate microprojection member coating apparatus 70 comprised of a container 76 holding the coating liquid 74. A pump 72 is provided to pump the coating liquid 74 through conduit 78. Upon emerging from conduit 78, the thickness of the coating liquid is controlled using a secondary roller 77 and doctor blade 79 similar to that shown in FIG. 5. The coating liquid then flows downwardly over inclined liquid holding surface 73 to the coating transfer region 75. An appropriate microprojection member conveying means (not shown in FIG. 7) conveys the web 42 of microprojection members 10 parallel to surface 43 whereby the microprojections are coated with the coating liquid. In this embodiment, the liquid holding surface is stationary rather than moving as shown in the FIG. 3–6 embodiments.

FIGS. 9 and 10 disclose an alternate coating apparatus according to the present invention. The coating apparatus disclosed in FIGS. 9 and 10 is similar to that disclosed in FIGS. 3–5 except that the cylindrically shaped coating drum has a plurality of grooves 129 therein. The coating liquid 124 is carried within the grooves of the rotating drum 122 as best shown in FIG. 10. The microprojection member 110 having a plurality of microprojections 112 is conveyed past the rotating drum 122 so that the microprojections 112 are aligned with the grooves 129. In this embodiment, the microprojections 112 must be aligned in discrete rows, so that each row is conveyed through a separate groove 129.

Figure 11:
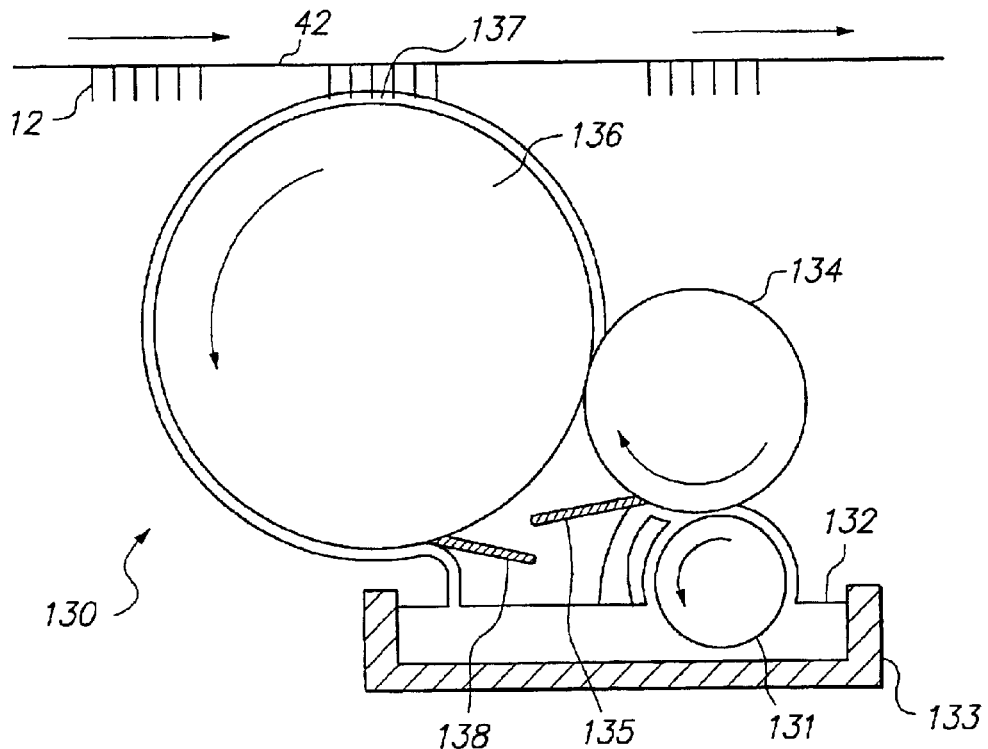
FIG. 11 is a side view, shown partly in section, of another apparatus according to the present invention.
Figure 12:
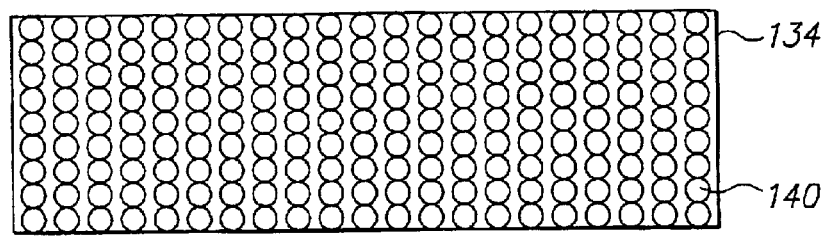
FIG. 12 is a side view of the anilox roller 134 shown in FIG. 11.

The microprojection member coating apparatus 130 shown in FIG. 11 is similar to the coating apparatus shown in FIG. 5 with the following differences. A fountain roller 131 brings the coating liquid 132 up to an anilox roller 134. The excess solution is wiped off the anilox roller 134 by a first doctor blade 135. The excess solution is then returned to the container 133. The anilox roller 134 meters the amount of solution transferred to the drum 136. The solution is carried by the drum 136 up to the coating transfer region 137 where it is coated onto the tips of the microprojections. The excess solution is removed from the drum 136 by means of a second doctor blade 138. The dimpled surface of the anilox roller 134 is best shown in FIG. 12. The dimples or cells 140 are equal in size and equally spaced on the surface of the anilox roller.

The coating liquids used in the present invention are typically solutions or suspensions of the pharmacologically active agent, most typically aqueous solutions or suspensions. The coating liquids preferably have a viscosity of about 5 to 500 centipoise (cP), and more preferably about 20 to 50 cP, when measured at a temperature of 25° C. and a shear strain rate of 100 $sec^{-1}$, in order to effectively coat the tiny stratum corneum-piercing elements to an appropriate thickness. The desired thickness of the solid coating on the microprojections is dependent upon the density of the microprojections per unit area and the viscosity and concentration of the coating composition as well as the coating method chosen. In general, coating thickness must be less than 50 $\mu$m since thicker coatings have a tendency to slough off the microprojections upon stratum corneum piercing. Preferred coating thicknesses are less than 10 micrometers as measured from the microprojection surface. Generally coating thickness is referred to as an average coating thickness measured over the coated microprojection. More preferred coating thicknesses are about 0.1 to 10 micrometers.

The kinetics of the agent-containing coating dissolution and release will depend on many factors including the nature of the agent, the coating process, the coating thickness and the coating composition (e.g., the presence of coating formulation additives). Depending on the release kinetics profile, it may be necessary to maintain the coated microprojections in piercing relation with the skin for extended periods of time (e.g., up to about 8 hours). This can be accomplished by anchoring the microprojection member to the skin using adhesives or by using anchored microprojections such as described in WO 97/48440, incorporated by reference in its entirety.

The apparatus and method of the present invention have particular utility with coating high potency agents requiring a dose of about 1 mg or less, preferably about 0.25 mg or less. Amounts within this range can be coated onto a microprojection array of the type shown in FIG. 1 having the sheet 12 with an area of up to 10 cm$^2$ and a microprojection density of up to 500 microprojections per cm$^2$ of the sheet.

Preferred drugs include desmopressin, luteinizing hormone releasing hormone (LHRH) and LHRH analogs (e.g., goserelin, leuprolide, buserelin, triptorelin), PTH, calcitonin, vasopressin, deamino [Val4, D-Arg8] arginine vasopressin, interferon alpha, interferon beta, interferon gamma, menotropins (urofollotropin (FSH) and leutinizing hormone (LH), erythrepoietrin (EPO), GM-CSF, G-CSF, IL-10, and glucagon. Preferred vaccines include vaccines for Lyme disease, influenza, hepatitis, hemophilus influenza B, tetanus, typhoid, mumps, measels, rubella, and pertusis.

In all cases, following coating, the coating solution is dried onto the microprojections by various means. In a preferred embodiment the coated device is dried in ambient room conditions. However, various temperatures and humidity levels can be used to dry the coating solution onto the microprojections. Additionally, the devices can be heated, lyophilized, freeze dried or similar techniques used to remove the water from the coating.

Other known formulation adjuvants can be added to the coating solution as long as they do not adversely affect the necessary solubility and viscosity characteristics of the coating solution and the physical integrity of the dried coating.

The following examples are given to enable those skilled in the art to more clearly understand and practice the present invention. They should not be considered as limiting the scope of the invention but merely as being illustrated as representative thereof.

EXAMPLE 1

A 31.0% (w/v) aqueous solution of ovalbumin was prepared by mixing for 1 hour 6.2 grams of ovalbumin (from chicken eggs, crystallized and lyophilized, salt free, sold by Sigma Chemical Co., St. Louis, Mo.) with 13.8 mL of sterile water. A 1.5% (w/v) aqueous solution of hydroxyethyl cellulose was prepared by mixing for 1 hour 0.15 g of the hydroxyethyl cellulose with 9.85 mL of sterile water. In a container were added, 6.65 mL of the ovalbumin solution, 1.40 mL of the hydroxyethyl cellulose solution, 0.26 mL of a 0.2M aqueous solution of fluorescein (a fluorescent dye used to make the coating solution, and the resultant dried coating, fluorescent) and 2.0 mL of sterile water and mixed for 1 hour. The resulting 20% ovalbumin, 0.2% hydroxyethyl cellulose, 0.005 M fluorescein solution had a viscosity of about 22 cP at a temperature of 25° C. and a rate of shearing strain of 100 sec$^{-1}$.

The coating of the microprojection arrays was done using an apparatus similar to that illustrated in FIG. 3. The rotating drum had a diameter of 3.78 cm (1.49 inches). The drum was used with a coating liquid container in the form of a cylindrical trough having a diameter of 4.06 cm (1.6 inches). The drum was driven by an electric motor to turn at a rotational speed of about 2 rpm and a drum surface speed of about 23.8 cm/minute (9.36 inches/minute). The track was adjusted relative to the drum so that the sled cleared the top of the rotating drum by 0.30 mm (0.012 inches). The doctor blade was positioned so that its knife edge was spaced 0.30 mm (0.012 inches) from the drum's surface. 3 mL of the coating solution was added to the coating liquid container.

The microprojection arrays were in the form of etched and punched titanium foils, the foils having a thickness of 30 um, a width of 2.7 cm (1.07 inches) and a length of 11.5 cm (4.54 inches). The microprojections had a triangular shape (60° tip angle) and a length (measured from the surface of the foil sheet to the tip of the bent triangularly-shaped microprojections) of 250 um (0.010 inches). The arrays were attached to a sled, oriented so that the microprojections were extending away from the sled and toward the rotating drum, by means of a partial vacuum applied through openings in the side of the sled facing the rotating drum. A partial vacuum of about 0.84 atm (25 inches Hg) was applied.

The sled was propelled along the track by a spur gear mounted on the same shaft as the drum. The gear engaged a rack on the sled. The gear governed the speed of the sled along the track which was 23.9 cm/minute (9.42 inches/minute).

The microprojections extending from the sheet of the microprojection array were coated to a depth of approximately 100 um (0.004 inches). Because the coating contained fluorescein dye, the coating depth was measured using a microscope having a lamp emitting light in the UV range.

EXAMPLE 2

Coating experiments were performed using the device shown in FIG. 3 and described herein. Increased amounts of a model drug (sucrose) coated on the microprojection array was observed as a function of coating time. The coating solution was an aqueous solution containing 50 wt % sucrose as a model drug and had an initial volume of 2 mL. The microprojection arrays being coated were in the form of a circular metal sheet having an area of 2 cm$^2$. The microprojection arrays were composed of titanium, had microprojection lengths of 250 $\mu$m, and a microprojection density of 321 microprojections/cm$^2$. The microprojections were tip coated in varying temperature and humidity conditions during operation of the coating device. Coatings were performed continuously for 70 minutes. The sucrose concentration in the coating solution was measured every 10 minutes. The results of the coating solution concentration vs. time are plotted in FIG. 14. The amount of sucrose coated per array was measured and plotted as a function of time in FIG. 15.

Figure 14:
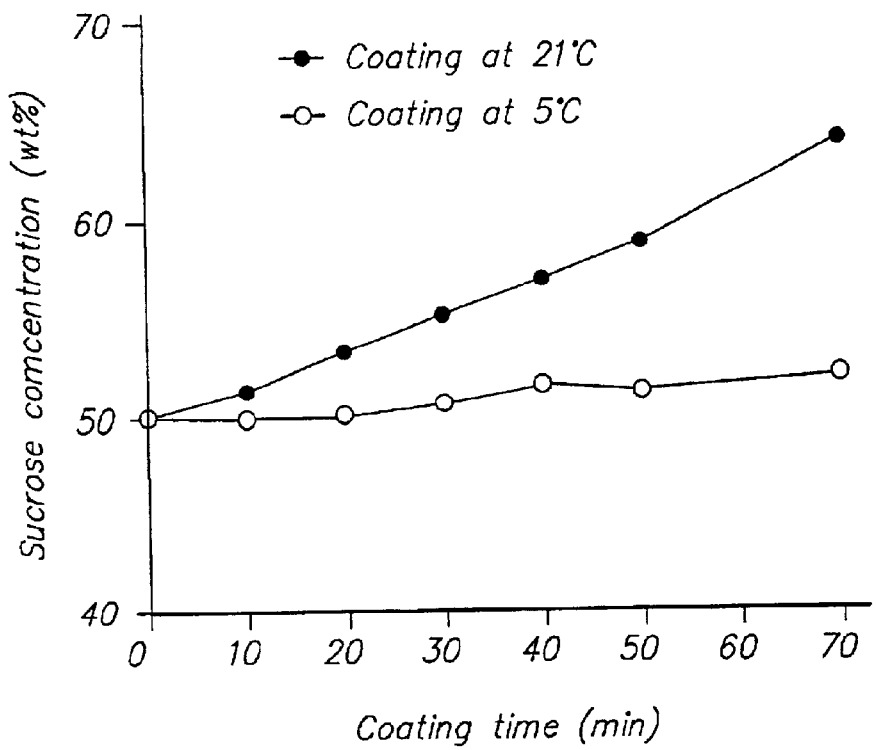
FIG. 14 is a graph of sucrose concentration versus time during coating at varying temperature and humidity conditions.
Figure 15:
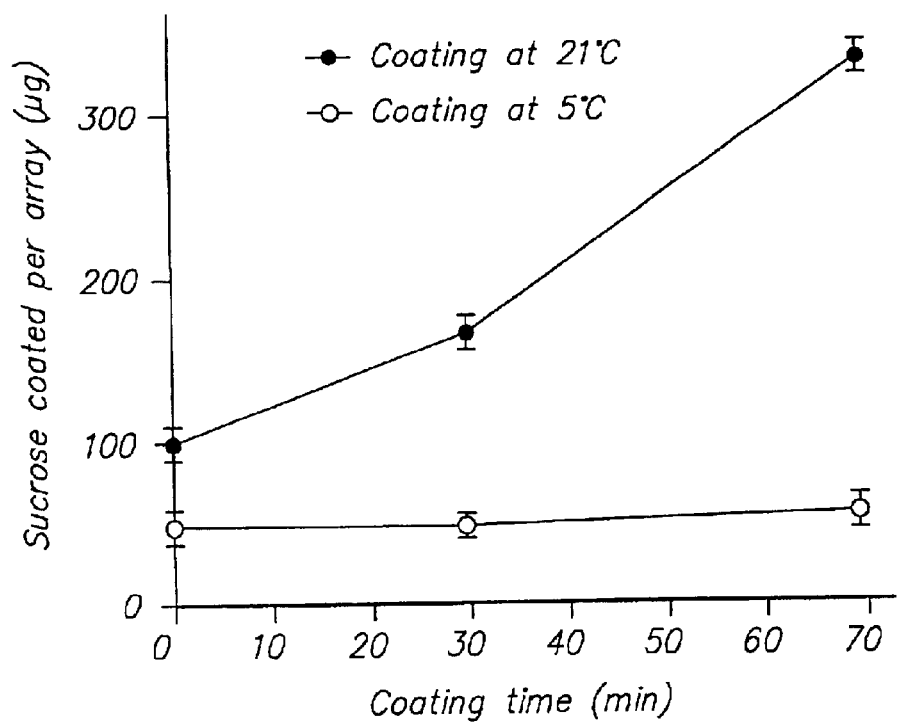
FIG. 15 is a graph of amount of sucrose coated on microprojection arrays at varying temperature and humidity conditions.

In the first study, coating was conducted at ambient conditions (21° C., 42% relative humidity). As shown in FIG. 14, there was an increase in sucrose concentration in the coating solution as a function of time during operation of the coating device. Analysis of the dried coatings on the microprojection tips revealed that the amount of sucrose coated increased as a function of time in ambient conditions (see FIG. 15).

In the second study, coating was conducted at 5° C. and 65% relative humidity. This resulted in stable sucrose concentration during the entire duration (70 min) of the coating experiment (see FIG. 14). Analysis of the dried coatings on the microprojection tips revealed that the amount of sucrose coated was constant in cold and higher relative humidity conditions (see FIG. 15).

This experiment demonstrated that significant water evaporation was taking place in ambient conditions and that this could be minimized by conducting the coating process at lower temperature and/or higher relative humidity than in ambient conditions. Alternatively, the coating process can be conducted using a chilled coating liquid to limit evaporative loss.

Figure 16:
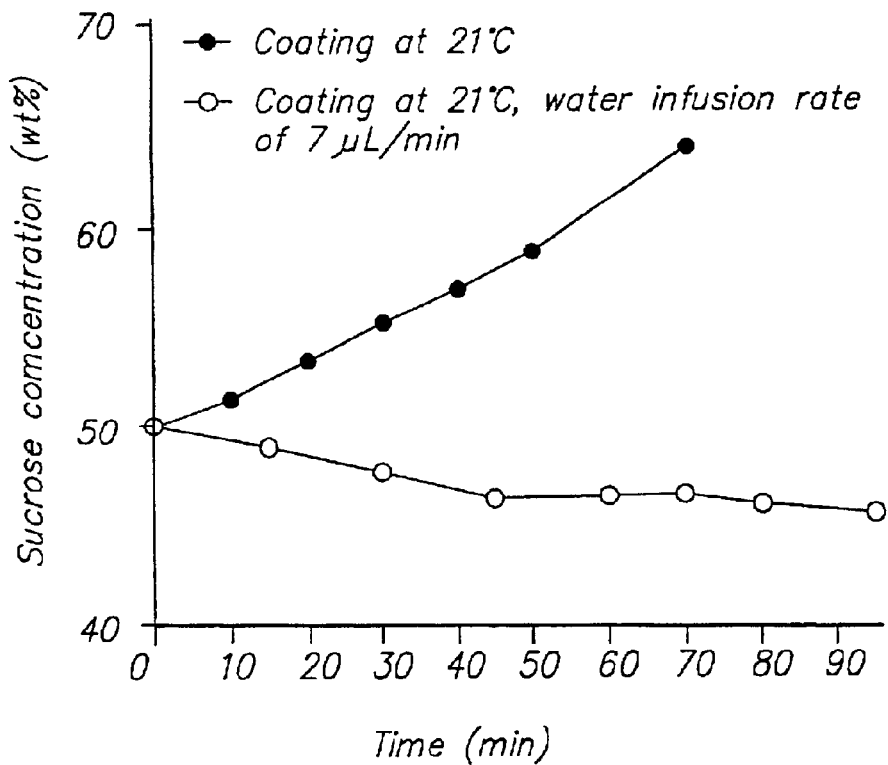
FIG. 16 is a graph of sucrose concentration versus time showing the effect of water infusion during coating at ambient temperature.

In a third study at ambient conditions (21° C., 42% relative humidity), the increase in sucrose concentration as a function of coating time was minimized by constant infusion of 7 μl/min water (this water infusion rate had been calculated from the increase in sucrose concentration) into the coating solution. The results are shown in FIG. 16. Overall, these experiments demonstrate that the evolution of the coating solution is linked to evaporation of water from the coating solution. This increase in concentration is detrimental to coating reproducibility that is desirable for pharmaceutical products. This negative effect can be minimized by performing the coating process at lower temperature, at increased relative humidity, by injection of solvent (water) in the drug coating solution reservoir, and/or combinations thereof, to compensate for the solvent evaporation.

EXAMPLE 3

Coating experiments were performed with several drugs and model compounds using the coating apparatus shown in FIG. 3 and described herein.

Figure 17:
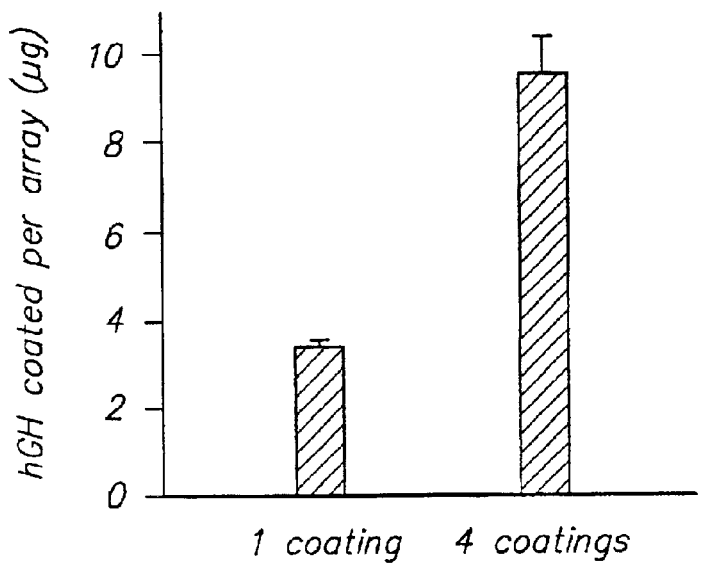
FIG. 17 is a graph showing the amounts of human growth hormone coated on microprojection arrays using single and multiple coatings.

Microprojection arrays were coated in cold conditions with the protein human growth hormone (hGH). Microprojection arrays (titanium sheets, microprojection lengths of 250 μm, microprojection density of 321 microprojections/cm$^2$, 2 cm$^2$ disc) were tip coated at 5° C. and 65% relative humidity using a 1.7 mL volume of a 20 wt % hGH, 20 wt % sucrose coating solution. Following one coating, analysis revealed that each array was coated with 3.3±0.2 μg hGH. A similar coating experiment was performed except that the microprojection arrays were coated four times with a cycle time of 5 seconds (i.e., each array was coated every five seconds). Analysis revealed that each array was coated with 9.5±0.9 μg hGH (FIG. 17). Scanning electron microscopy (SEM) of the arrays coated once and four times revealed good uniformity of coating from microprojection to microprojection with the coating limited to the tip (i.e., to the leading 120 μm) of the entire 250 μm microprojection length. This experiment demonstrated that multiple coatings could be used to increase the drug loading on the microprojection array.

Figure 18:
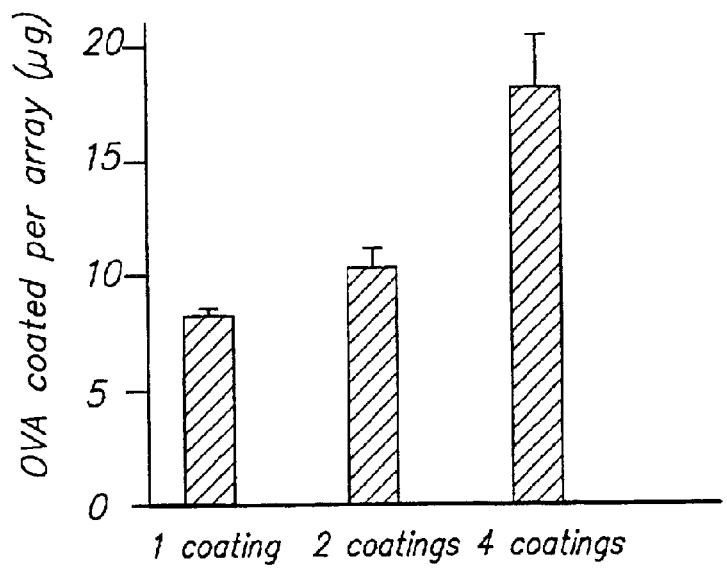
FIG. 18 is a graph showing the amounts of ovalbumin coated on microprojection arrays using single and multiple coatings.

Additional work was performed with the model protein ovalbumin (OVA) in order to evaluate the effect of multiple coating cycles in ambient conditions. Microprojection arrays (titanium sheets, microprojection lengths of 250 μm, microprojection density of 321 microprojections/cm$^2$, 2 cm$^2$ disc) were tip coated at 21° C. and 46% relative humidity using a 2 mL volume of a 20 wt % OVA aqueous coating solution. Microprojection arrays were coated 1, 2 or 4 times with a coating cycle of 5 seconds. Like in the previous experiment, increased coating amounts were obtained with an increase in the number of coatings (see FIG. 18). Also, SEM of the arrays revealed good uniformity of coating from microprojection to microprojection with the coating limited to the leading 120 μm tips of the microprojections.

Figure 19:
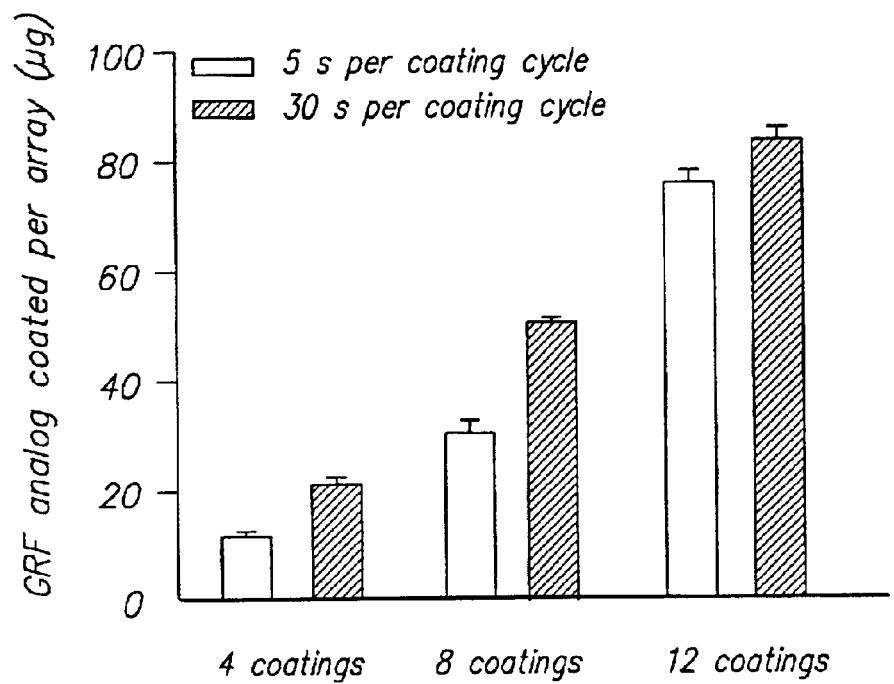
FIG. 19 is a graph showing amounts of GRF analog coated on microprojection arrays using multiple coatings and varying coating cycles.

Additional work was performed with the peptide growth hormone releasing factor analog (GRF) in order to evaluate the need for intermediate drying between cycles in ambient conditions. Microprojection arrays (titanium sheets, microprojection lengths of 200 μm, microprojection density of 321 microprojections/cm$^2$, 2 cm$^2$ disc) were tip coated at 21° C. and 46% relative humidity using the coating apparatus shown in FIG. 3 and described herein using 1.5 mL of a 7.5 wt % GRF aqueous coating solution. Microprojection arrays were coated 4, 8 or 12 times with coating cycles of 5 and 30 seconds (12 coatings were performed in 1 minute and 6 minutes with 5 second and 30 second coating cycles, respectively). Analysis of the microprojection arrays (5 arrays per condition) demonstrated good reproducibility of coating in all conditions with a trend toward decreased variability with increased number of coatings. The amount of GRF increased with the number of coatings with both coating cycle times. Higher coating levels were obtained with the longer coating cycle but the effect was surprisingly small (see FIG. 19). SEM of the arrays revealed good uniformity of coating from microprojection to microprojection with the coating limited to the leading 120 μm tips of the microprojections.

Overall, these experiments demonstrate that the coating cycle time can be shorten to as low as 5 seconds, which improves manufacturing.

What is claimed is:

1. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth; and immersing the microprojections to a predetermined level in said coating liquid disposed at said coating transfer region, wherein the microprojections have a length, as measured from a surface or edge of the substrate, which is greater than said predetermined depth of said coating liquid at said coating transfer region.

2. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth; and immersing the microprojections to a predetermined level in said coating liquid disposed at said coating transfer region, wherein the microprojections have a length, as measured from a surface or edge of the substrate, which is greater than said predetermined depth, and wherein the depth of said coating liquid at said coating transfer region is greater than said microprojection immersion level.

3. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid holding surface, said liquid-holding surface having a coating transfer region;

conveying said coating liquid onto said liquid-holding surface;

controlling the depth of said coating liquid at said coating transfer region to a predetermined depth; and immersing the microprojections to a predetermined level in said coating liquid disposed at said coating transfer region.

4. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid holding surface, said liquid-holding surface having a coating transfer region;

conveying said coating liquid onto said liquid-holding surface by rotating a portion of said roller through a bath of said coating liquid;

controlling the depth of the coating liquid at the coating transfer region to a predetermined depth; and immersing the microprojections to a predetermined level in said coating liquid disposed at said coating transfer region.

5. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid holding surface, said liquid-holding surface having a coating transfer region;

conveying said coating liquid onto said liquid-holding surface by rotating a portion of said roller through a bath of said coating liquid;

controlling the depth of said coating liquid at said coating transfer region to a predetermined depth by controlling the rotational speed of said roller; and immersing the microprojections to a predetermined level in said coating liquid disposed at said coating transfer region.

6. A method of coating a liquid onto a plurality of microprojections extending from a surface or edge of a substrate substantially without coating the liquid onto the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth; and immersing the microprojections to a predetermined level in said coating liquid disposed at said coating transfer region, wherein said step of immersing of the microprojections is accomplished by conveying the substrate along a predetermined pathway adjacent said coating transfer region.

7. A method of coating a liquid onto a plurality or microprojections extending from a surface or edge of a substrate substantially without coating the liquid onto the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth; and immersing the microprojections to a predetermined level in said coating liquid disposed at said coating transfer region, wherein said step of immersing of the microprojections is accomplished by continuously conveying a web comprised of a plurality of the substrates along a predetermined pathway adjacent said coating transfer region.

8. A method of forming a solid coating on a plurality of microprojections extending from a surface or edge of a substrate without forming a coating on the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth;

immersing the microprojections to a predetermined level in said coating liquid disposed at said coating transfer region;

removing the microprojections from said coating liquid; and drying the coating liquid coated on the microprojections thereby forming a solid agent-containing coating on the microprojections.

9. A method of forming a solid coating on a plurality of microprojections extending from a surface or edge of a substrate without forming a coating on the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth;

immersing the microprojections to a predetermined level in said coating liquid disposed at said coating transfer region;

removing the microprojections from said coating liquid; and drying the coating liquid coated on the microprojections thereby forming a solid agent-containing coating on the microprojections; and repeating said immersing, removing and drying steps to provide multiple layers of said solid agent-containing coating.

10. A method of forming a solid coating on a plurality of microprojections extending from a surface or edge of a substrate without forming a coating on the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth;

immersing the microprojections to a predetermined level in said coating liquid disposed at said coating transfer region;

removing the microprojections from said coating liquid; and drying the coating liquid coated on the microprojections thereby forming solid agent-containing coating on the microprojections, wherein said agent comprises a drug or a vaccine and the liquid comprises water.

11. A method of forming a solid coating on a plurality of microprojections extending from a surface or edge of a substrate without forming a coating on the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth;

immersing the microprojections to a predetermined level in said coating liquid disposed at said coating transfer region;

removing the microprojections from said coating liquid; and drying the coating liquid coated on the microprojections thereby forming solid agent-containing coating on the microprojections, wherein said coating liquid comprise a liquid solvent and said agent, wherein said coating liquid has an agent concentration, and wherein said agent concentration is controlled by a method selected from the group consisting of conducting said coating at a temperature which reduces evaporative loss of said liquid solvent, conducting said coating in an atmosphere containing sufficiently high amounts of gascous solvent to reduce evaporative loss of said liquid solvent, infusing liquid solvent into said coating liquid at a rate which compensates for evaporative loss of said liquid solvent, and combinations thereof.

12. A method of forming a solid coating on a plurality of microprojections extending from a surface or edge of a substrate without forming a coating on the substrate, comprising the steps of:

providing an agent-containing coating liquid;

providing a cylindrically shaped roller having a liquid-holding surface, the liquid holding surface having a coating transfer region;

conveying said coating liquid onto said liquid-holding surface;

controlling the depth of said coating liquid at said coating transfer region to a predetermined depth;

immersing the microprojections to a predetermined level in said coating liquid disposed at said coating transfer region;

removing the microprojections from said coating liquid; and drying the coating liquid coated on the microprojections thereby forming solid agent-containing coating on the microprojections, wherein said coating liquid comprises a liquid solvent and said agent, wherein said coating liquid has an agent concentration, and wherein said agent concentration is controlled by a method selected from the group consisting of conducting said coating at a temperature which reduces evaporative loss of said liquid solvent, conducting said coating in an atmosphere containing sufficiently high amounts of gaseous solvent to reduce evaporative loss of said liquid solvent, infusing liquid solvent into said coating liquid at a rate which compensates for evaporative loss of said liquid solvent, and combinations thereof, and wherein said liquid solvent comprises water, wherein said temperature is less than about 10° C., and wherein said atmosphere has a relative humidity greater than about 60%.

* * * * *